United States Patent [19]

Wallace

[11] Patent Number: Plant 7,195

[45] Date of Patent: Mar. 13, 1990

[54] WILLAMETTE CHESTNUT

[76] Inventor: Robert D. Wallace, Rte. 1, Box 341, Alachua, Fla. 32615

[21] Appl. No.: 206,876

[22] Filed: Jun. 13, 1988

[51] Int. Cl.[4] ..... A01H 5/00

[52] U.S. Cl. ..... Plt./30

[58] Field of Search ..... Plt./30

*Primary Examiner*—James R. Feyrer

[57] ABSTRACT

A medium size hybrid chestnut tree, having an upright and widely spreading form and glossy dark green foliage with prolific, sweet scented flowers appearing after leaf out in spring; the tree being a regular and very productive bearer of extremely large, chocolate brown, very sweet and easy-to-peel nuts, the nuts ripening and falling free from the burrs in mid-September; the tree also displaying a high genetic resistance to the chestnut bark blight (*Endothia parasitica*), being bred from the same line of hybrid chestnut trees as the Revival Chestnut (U.S. Plant Pat. No. 5,537), the Heritage Chestnut (U.S. Plant Pat. No. 6,574), and the Carolina Chestnut (U.S. Plant Pat. No. 7,041), the present variety itself not showing any instance of blight infection in 12 years of growth in the orchard.

1 Drawing Sheet

ORIGIN OF THE VARIETY

The present variety is an open-pollinated seedling of American×Chinese chestnut hybrids growing in the Chestnut Hill Nursery orchards in Alachua, Fla. These hybrid chestnut trees originated in a cross by my grandfather, Dr. Robert T. Dunstan, between flowering grafts of a native American chestnut (unpatented) found growing uninfected in a grove of dead and dying chestnuts, and a composite tree of 3 USDA released varieties of Chinese chestnut, Kuling, Meiling, and Nanking (all unpatented), in 1953 in North Carolina. Seedlings from this first cross were backcrossed to the parent trees. The second generation trees resulting from this cross were set out in the Chestnut Hill orchard. Nuts from the trees bearing the largest and sweetest nuts were planted. These third generation seedlings were grown in the nursery and then set out in the orchard. The present variety is an individual third generation seedling tree, exhibiting the best combination of characteristics necessary for commercial orchard production, that I have determined to be novel and distinct.

ASEXUAL REPRODUCTION OF THE VARIETY

Upon recognition of the excellent qualitites of the present variety, it was asexually reproduced by myself by grafting onto Chinese chestnut rootstocks (unpatented). In maturity, all such reproductions run true to the original tree in all respects.

SUMMARY OF THE VARIETY

The present variety of chestnut tree is of medium size, upright form with widley spreading branches, having an abundance of glossy, dark green, large, oblong leaves with rounded ends and a dentate margin, flowering prolifically after leafing out in the late spring, thus missing late freezes that would hurt nut production; the tree bearing at a young age and regularly every year, the tree being a very productive bearer of extremely large, chocolate brown nuts, almost always 3 per burr, the nuts ripening in mid-September, and having a large percentage of the nuts fall free from the burr, which is very important for mechanical harvesting. The pellicle is thin and easily released from the kernel, which is crucial for commercial peeling and processing operations. The kernel is a light white color and excellent in taste, being very sweet even raw and uncured, and is delicious when steamed or roasted.

The present variety can be distinguished from the Revival Chestnut (U.S. Plant Pat. No. 5,537), which was bred from the same family of hybrid chestnuts, by its much larger sized and darker colored nuts, and its more widely spreading form. The present variety can be distinguished from the Heritage Chestnut (U.S. Plant Pat. No. 6,574) especially by its nuts, which are several times as large, and its tree form, which is much more spreading instead of straight-bolded and timber form, and its leaves, which have a much more smooth margin than the deeply dentate margins of 'Heritage'. The present variety produces nuts that ripen earlier than 'Heritage', and loses its leaves later in the season. The present variety can be distinguished from the Carolina Chestnut (U.S. Plant Pat. No. 7,041), to which it most resembles, by its much larger and more rounded nuts, and its shorter stature and more widely spreading tree form, spreading almost as wide as it is tall. The present variety shows a high degree of blight resistance, having not shown any infection from the disease in over 12 years of growth in the orchard. It is also characterized by having a wide range and is capable of growing well and producing nuts from southern New England to north Florida. It is well suited to the cool, damp winters and hot summers of the Pacific Coast. The tree exhibits the particular combinations of characteristics that is desirable for commercial production of nuts. It has both good tree form and the blight resistance necessary for orchard growth in many regions, and has the heavy production of large, excellent tasting, easy-to-peel nuts that is important for marketing.

BRIEF DESCRIPTION OF THE DRAWING

The drawing is an illustration, by photographic reproduction in color, of a twig with leaves and catkins and nuts out of the burrs.

DESCRIPTION OF THE VARIETY

The botanical details of this new and distinct variety of chestnut tree — with color definitions (except those in common color terms) referenced to *Maerz and Paul Dictionary of Color* — are as follows:

Tree:

*Size (at maturity).*—Medium, reaching a height of approximately 40–50 feet and a spread of 30 feet.

*Vigor.*—Vigorous, attaining a height of 25 feet and a spread of 18 feet in 12 years of growth at its location near Alachua, Fla.

Trunk:

*Form.*—Upright with widely spreading branches, growing in a modified central leader form in its present location in an open field.

*Texture.*—Smooth.

*Color of bark.*—Gray (21-A-1).

Branches:

*Form.*—Strong.

*Texture.*—Smooth.

*Lenticels.*—Few, small.

*Branching habit.*—Widely spreading, with the first scaffold branches beginning 4 feet above the ground, and typical lower crotch angles averaging 80 to 90 degrees.

*Color.*—New wood: Greenish gray (13-F-3). Mature wood: Gray (21-A-1).

Foliage:

*Quantity.*—Abundant.

*Density.*—Dense.

Leaves:

*Size.*—Large. Average length: 6–8" (including petiole). Average width: 2".

*Shape.*—Oblong with rounded tip and base.

*Thickness.*—Thick.

*Texture.*—Smooth on top, with fine tomentous hairs underneath.

*Margin.*—Dentate, with shallow dentations.

*Petiole.*—Length: Medium. Thickness: Medium.

*Color.*—Top side — Glossy dark green (30-A-12). Under side — Lighter green (21-G-7).

Bloom:

*Amount of bloom.*—Heavy.

*Color.*—Yellow white (18-B-1).

*Blooming period.*—Late. After leaf out in April.

*Age at which tree starts flowering.*—Early; 2–3 years after graft placement.

Crop:

*Bearing.*—Regular (yearly) bearer.

*Productivity.*—Very heavy.

*Ripening period.*—Short. September 10–September 20.

*Distribution of nuts on tree.*—Well distributed.

*Tenacity.*—Burrs split as the nuts ripen. Responds well to shaking.

Hull:

*Description.*—Round burr with dense, short spines.

*Size.*—4–5" in diameter.

*Number of nuts.*—Almost always 3 per burr.

*Dehiscence.*—A high percentage of the nuts easily released for harvesting. Easy to remove remaining nuts from the burr.

*Color.*—Brown (15-A-10).

Nut:

*Size.*—Extremely large. Average size: $1\frac{1}{2}'' \times 1\frac{1}{4}''$. Average weight: 18–22 nuts per pound.

*Form.*—Broad and rounded on one side, flat on other side.

*Blossom end.*—Rounded tip.

*Basal end.*—Flattened.

*Color.*—Chocolate brown (8-L-12).

*Shell.*—Thin, yet does not split.

*Hardness of shell.*—Firm.

*Texture of shell.*—Smooth.

*Percentage of kernel to nut.*—Very high (95%).

Kernel:

*Size.*—Almost as large as nut size.

*Form.*—Same as nut shape.

*Pellicle.*—Thin, very easy to remove, even fresh and uncured.

*Flavor.*—Very sweet with excellent flavor.

*Color.*—Yellow white (11-B-1).

Resistance to insects: No unusual susceptibilities noted.

Resistance to disease: High genetic resistance to chestnut bark fungus (*Endothia parasitica*), no other susceptibilities to any other disease.

The chestnut tree and its nuts herein described may vary in slight detail due to climatic and soil conditions under which the variety may be grown; the present description being of the variety as grown in Alachua, Fla.

I claim:

1. A new and distinct variety of hybrid chestnut tree, substantially as illustrated and described, which is of medium size, upright and widely spreading form, with large, glossy, dark green oblong leaves with dentate margins, flowering late and profusely after leaf out in spring; the tree being a regular and very prolific bearer of extremely large, chocolate brown, very sweet and easy-to-peel nuts that ripen in mid-September and are released easily from the burrs for easy harvesting; the trees showing a high genetic resistance to the chestnut bark blight; and the trees being especially characterized by having the combination of good orchard form, blight resistance.

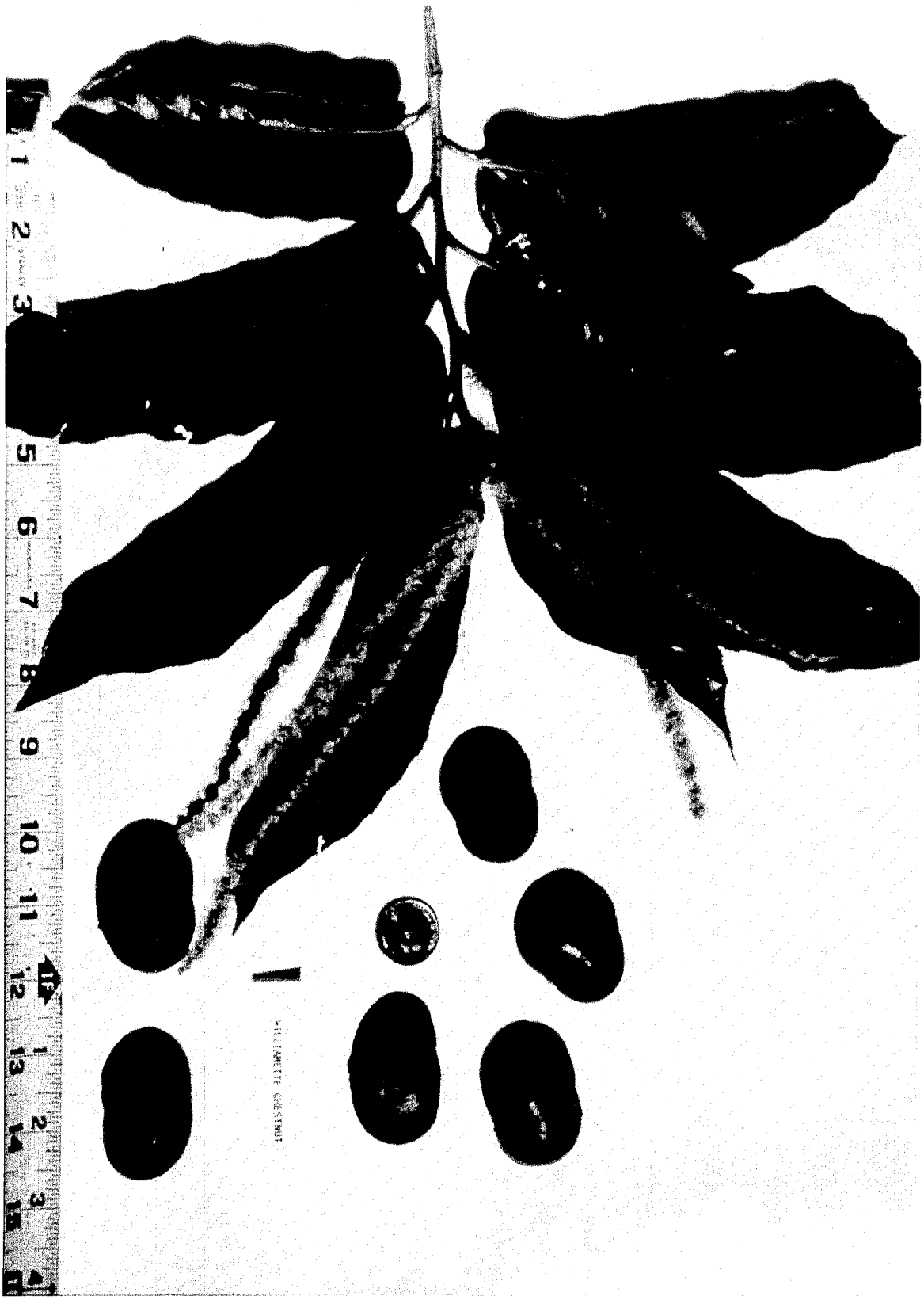

* * * * *